(12) United States Patent
Martin (10) Patent No.: US 10,463,449 B2
(45) Date of Patent: Nov. 5, 2019

(54) TORQUE LIMITING DENTAL TOOL HOLDER

(71) Applicant: STRAUMANN HOLDING AG, Basel (CH)

(72) Inventor: Boris Martin, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 63 days.

(21) Appl. No.: 15/556,788

(22) PCT Filed: Mar. 9, 2016

(86) PCT No.: PCT/EP2016/054968
§ 371 (c)(1),
(2) Date: Sep. 8, 2017

(87) PCT Pub. No.: WO2016/142403
PCT Pub. Date: Sep. 15, 2016

(65) Prior Publication Data
US 2018/0055599 A1    Mar. 1, 2018

(30) Foreign Application Priority Data
Mar. 9, 2015 (EP) .................................... 15158214

(51) Int. Cl.
*A61C 1/18* (2006.01)
*A61C 8/00* (2006.01)

(52) U.S. Cl.
CPC ............ *A61C 1/186* (2013.01); *A61C 8/0089* (2013.01)

(58) Field of Classification Search
CPC ......... A61C 1/186; A61C 8/0089; A61C 1/18; B25B 23/1427; B25B 23/141; B25B 23/14; B25B 23/142; B25B 13/48
See application file for complete search history.

(56) References Cited

U.S. PATENT DOCUMENTS 5,158,458 A  *  10/1992  Perry .................... A61C 8/0089
                                                              433/141
5,337,638 A       8/1994  Coss et al.
                      (Continued)

FOREIGN PATENT DOCUMENTS

DE    20 2004 014195 U1    11/2004

OTHER PUBLICATIONS

May 20, 2016 Search Report issued in International Patent Application No. PCT/EP2016/054968.
(Continued)

*Primary Examiner* — Robert J Scruggs
(74) *Attorney, Agent, or Firm* — Oliff PLC (57) ABSTRACT

A torque limiting device for use with a dental drive tool including a housing defining a rotation axis and having a bore concentric with the rotation axis and a torque limiting insert. The housing has a recess for housing at least part of the torque limiting insert. The torque limiting insert includes a fixing region held within the housing and a spring region extending from the fixing region and including a locking catch protruding into the bore. The locking catch is aligned with the recess so it can be moved radially outwards into the recess in to a disengaged position. The locking catch is arranged to engage with the dental drive tool when the tool is introduced in the bore to transmit a torque applied to the housing and to deflect into the disengaged position against the force of the spring region when a predefined torque limit is reached.

17 Claims, 3 Drawing Sheets

(56) References Cited

U.S. PATENT DOCUMENTS

| | | | |
|---|---|---|---|
| 5,368,480 A * | 11/1994 | Balfour | A61C 8/0089 |
| | | | 433/141 |
| 5,734,113 A | 3/1998 | Vogt et al. | |
| 6,382,051 B1 | 5/2002 | Chang | |
| 6,868,759 B2 | 3/2005 | Tuan-Mu | |
| 7,011,001 B2 | 3/2006 | Knox et al. | |
| 2005/0072277 A1 | 4/2005 | Knox et al. | |
| 2008/0070190 A1* | 3/2008 | Baumgartner | B25B 13/463 |
| | | | 433/141 |
| 2008/0178714 A1 | 7/2008 | Gross | |

OTHER PUBLICATIONS

May 20, 2016 Written Opinion issued in International Patent Application No. PCT/EP2016/054968.

* cited by examiner

TORQUE LIMITING DENTAL TOOL HOLDER

The present invention relates to a torque limiting device for use with a dental drive tool according to the preamble of claim 1 and a torque limiting kit comprising such a torque limiting device according to claim 17.

In the field of implant dentistry dentists and dental technicians often have to fasten connection elements, namely screws, abutments or other secondary parts, to dental implants or implant analogs.

During the creation of a dental crown or bridge the dental technician usually attaches an abutment to an implant analog in a plaster model of the patient's mouth using an abutment, or basal, screw. The dental prosthesis is then built on top of the abutment.

At present, the undefined instruction to "hand tighten" the abutment screw is given to the dental technician, which can easily result in over-tightening. Over-torquing in the dental lab can lead to failures chairside, when the same abutment screw is used to fasten the finished abutment to the implant at higher torque.

Dental torque wrenches in the form of a ratchet can be equipped with a torque indicator to control the torque applied to a screw. Document U.S. Pat. No. 5,734,113 discloses a surgical torque wrench including a torque instrument and a torque indicator mountable on the torque instrument. The torque is generated by application of force to a free end of a bending rod indirectly secured at its other end to the torque wrench and the deflection of the bending rod indicates the torque intensity.

Dental torque wrenches with a mechanical torque limitation are also known and usually provided with a mechanism that possesses a pivotable lever or a rotatable catch on the ratchet head, so that the force of a pretensioned compression spring is overcome when the permissible torque is exceeded and the lever is thus bent or the catch comes out of engagement to prevent further torque transmission. Documents U.S. Pat. Nos. 7,011,001, 6,868,759 and 5,337,638 disclose examples of such wrenches.

Document U.S. Pat. No. 5,368,480 discloses a dental implant wrench having a specified torque limit defined by the shear resistance of cams projecting from a hub arranged in the torque limit control structure of the wrench. The torque applied to the wrench is transmitted to a driver that will shear one of these cams once the specified torque limit has been reached. This shearing will be felt by the dental technician who can stop torquing. Once all the cams have been sheared the hub must be replaced.

Document U.S. Pat. No. 5,158,458 discloses another system in which the torque is limited by incorporating an insert in the torque transmission structure which breaks when the specified torque limit has been reached.

Although these different torque limiting wrenches meet the desired functional requirements, these tools have a complex construction containing numerous intricate moving components. Moreover some of these tools include components that must be replaced after use, rendering these tools expensive and burdensome. Further, many torque wrench limiters do not maintain their calibration after continuous use and require a regular maintenance.

In order to fasten abutments into implant analogs and other holding devices dental technicians need a handy inexpensive dental torque wrench which requires minimum calibration or maintenance and that disengages from the screw usually at a torque of approximately 8 to 10 Ncm. At this torque it is possible to work with the abutment without placing too great a strain on the abutment screw.

The object of the present invention is therefore to make available a torque limiting device with a very simple design and a kit comprising this torque limiting device.

This object is achieved by a torque limiting device according to claim 1 and a kit according to claim 17.

Preferred embodiments are the subject matter of the dependent claims.

According to one aspect the present invention provides a torque limiting device for use with a dental drive tool comprising a housing defining a rotation axis and having a bore concentric with the rotation axis and a torque limiting insert, the housing having a recess perpendicular to and in communication with the bore for housing at least a part of the torque limiting insert, the torque limiting insert comprising a fixing region held within the housing in a non-rotatable manner and a spring region extending from the fixing region and comprising a locking catch, said locking catch protruding into the bore in a resting position, and being aligned with the recess such that the locking catch can be moved at least approximately radially outwards with respect to the rotation axis into the recess in to a disengaged position, wherein the locking catch is arranged to engage with the dental drive tool when the tool is introduced in the bore in order to transmit a torque applied to the housing to the tool and to deflect into the disengaged position against the force of the spring region when a predefined torque limit has been reached.

The device of the present invention therefore provides a torque limiting device free from moving parts. Instead the housing and insert remain in a fixed relationship. This greatly simplifies the manufacture and maintenance of the device. The torque limit is provided by the locking catch of the torque limiting insert, which will be deflected out of torque transmitting engagement with the drive tool once a predetermined torque limit is reached. The flexibility and resilience of the torque limiting insert means that torque transfer is limited without damage to the device, thus enabling it to be used indefinitely without the need for replacement parts.

Although it is possible for the device to house a plurality of torque limiting inserts such that a plurality of locking catches protrude into the bore, it is preferred that the device comprises a single torque limiting insert having a single locking catch. This keeps the complexity of the device to a minimum.

In its simplest and most preferred embodiment the torque limiting device consists only of the housing and the torque limiting insert. No further components are required in order to achieve the desired torque limitation.

The bore in the housing is intended to directly receive the drive tool. By directly it is meant that there is no third element between the tool and the housing to receive and/or retain the tool.

It is preferred that the bore of the housing comprises an abutment surface against which the drive tool can abut. This ensures that the tool cannot be inserted too far through the housing and therefore that the device and tool are in correct axial alignment. The abutment surface is preferably perpendicular to the rotation axis. In one embodiment the bore comprises an internal shoulder that forms the abutment surface. In a preferred embodiment however the bore is a blind bore, the end surface of the bore forming an abutment surface. This simplifies the construction of the housing.

Preferably the bore comprises an undercut for forming a snap-fit connection with the drive tool. The undercut can be formed by an annular groove in the bore or an annular protrusion, the undercut being created by the far side of the protrusion. In such embodiments the drive tool comprises a complementary protrusion. At least the protrusion of the drive tool (or, where present, the protrusion of the bore) is resilient such that this can be deflected and/or compressed to allow the tool to be inserted into the housing until the undercut of the bore and protrusion of the drive tool are brought into alignment, whereupon the protrusion springs back to, or towards, its original shape. This provides the user with physical feedback that the tool has been correctly inserted and the snap fit connection provides an axial retention between the device and the tool. This is beneficial both in that the device will not accidentally slip off the tool during use and further it enables the housing and tool to be transported as a unit until the housing is intentionally disconnected.

Snap fit connections are well known in the art and any known configuration can be applied between the housing and dental drive tool.

In one preferred embodiment the housing comprises a resilient lip at an open end of the bore. In another embodiment the bore comprises an annular groove on its interior wall, separate and axially remote from the recess, preferably in the region of an open end of the bore. Both of these embodiments enable the housing to form a snap fit connection with a complementary drive tool.

Preferably the housing is at least approximately in the form of a circular cylinder for an easy grip and rotation.

Optionally the lateral surface of the housing is a knurled or an otherwise textured surface to assist the user in securely gripping the device and preventing slipping during tightening.

Although the bore can be any shape necessary in order to receive the drive tool, e.g. frustoconical, in most embodiments the bore is circular cylindrical.

The recess formed in the housing is perpendicular to and in communication with the bore. It is used to accommodate at least a part of the torque limiting insert within the housing.

In one embodiment the recess comprises an annular groove extending about the interior wall of the bore. The recess can extend about the whole of the circumference of the bore or only a part of this. The groove comprises a back wall which delimits the radial depth of the groove. In other words the groove is closed in the radial direction and does not communicate with the exterior of the housing, although the radial depth of the groove can vary about its circumference.

In a preferred embodiment the recess comprises a slot open towards the exterior of the housing and limited in the circumferential direction by end walls. This enables easy insertion, and possibly removal, of the insert from the exterior of the housing. Once the insert is accommodated within the slot a cover or other closure means may be positioned within or over the slot to seal this.

The slot is preferably in the form of a circular segment preferably having an angle less than 180°. The end walls are preferably in a plane parallel to the diameter of the housing as this eases manufacturing.

In particularly preferred embodiment the recess comprises a slot open towards the exterior of the housing and limited in the circumferential direction by end walls and an annular groove extending about the interior wall of the bore in the plane of and in communication with the slot.

In this embodiment the annular groove preferably extends about an angle of more than 180° measured from one end wall of the slot to the other.

As mentioned above, the recess is perpendicular to the bore, that is to say, its central axis, when viewed in a cross-section in the plane of the rotation axis, is perpendicular to the rotation axis. In some embodiments the axially limiting walls of the recess may be sloped, stepped or curved. However, preferably the axially limiting walls of the recess are perpendicular to the rotation axis. This simplifies manufacturing.

The shape of the recess is governed by the torque limiting insert which is to be housed within it.

The torque limiting insert comprises a fixing region held within the housing in a non-rotatable manner.

In some embodiments the fixing region is located in a hollow in the housing which is not perpendicular to the bore but is in communication with the recess. Thus the hollow forms an extension to the recess located in a different plane. This hollow may, for example, extend in a plane parallel to the rotation axis and hence perpendicular to the recess. In preferred embodiments however the fixing region is held within the recess. This simplifies production of both the housing and the insert.

In preferred embodiments the fixing region comprises at least one abutment surface for abutting against a radially extending wall of the recess. This wall could be one of the end walls of the slot, as discussed above, or an end surface formed in an annular groove. For example, a closed groove may comprise a section having a greater radius than a neighbouring section. This change in radius will produce a radially extending wall against which the abutment surface of the fixing region can abut. For the avoidance of doubt, by "radially extending" it is meant that the wall must have a radial dimension, in other words, the first end of the wall has a different distance to the rotation axis than the second end. It is not required that the wall extends along a radial line from the rotation axis.

In some embodiments the fixing region may be welded, glued or otherwise permanently attached to the housing. However, it is preferred that the insert is held within the housing through a friction or form fit as this simplifies production. It also enables the insert to be removed from the housing and replaced if necessary. Most preferably the insert is held within the housing via an interference fit with the walls of the recess.

Therefore it is preferred that the fixing region comprises two abutment surfaces which abut against opposing radially extending walls of the recess. This prevents relative rotation of the insert with respect to the housing in either direction. For example, the fixing region may comprise an arm extending at least approximately radially outwards with respect to the rotation axis. This can be positioned within a slot or section of groove having an equal circumferential extent to the arm, such that both sides of the arm abut a wall of the recess.

In embodiments in which the recess comprises a slot limited in the circumferential direction by end walls, it is preferable that the fixing region comprises first and second abutment surfaces for abutment against said end walls. In a preferred embodiment the fixing region comprises first and second radially extending arms, each arm comprising an abutment surface. The first and second radially extending arms abut opposing end walls of the slot. In this way the arms can have a lesser circumferential extent that the slot, which eases insertion of the insert into the recess.

These arms can be designed so that their abutment surfaces align exactly with the end walls of the slot when the torque limiting insert is inserted in the recess, or alternatively the arms can be resiliently biased against the end walls of the slot, thus increasing the retentive force between the insert and housing.

The first and second radially extending arms preferably define a circle sector with respect to the rotation axis, preferably with a central angle of less than 180°.

Said arms preferably include distal ends which extend in a circumferential direction towards each other. Such arms allow for an easy manipulation of the torque limiting insert when it is inserted in or removed from the recess.

The spring region of the insert extends from the fixing region and comprises a locking catch. The spring region is housed in the recess, with at least the locking catch protruding into the bore. The locking catch is preferably located at a free end of the spring region, most preferably at the distal most part of the spring region, in order to maximize the amount of deflection possible.

The locking catch must be capable of being moved in a direction radially outwards from its resting position. This means that the recess must be shaped such that it is in alignment with the locking catch. This creates an area of open space behind the catch into which it can be deflected.

In a preferred embodiment the torque limiting insert comprises an open ring, the locking catch being located at one end and the fixing region being located at the opposing end. The fixing region can take the form of one or more radially extending arms as discussed above, comprising at least one abutment surface abutting an end wall of the recess. Alternatively the fixing region may comprise one or more axially extending arm or blade for accommodation in one or more hollow in the housing. When the insert comprises an open ring it is preferred that the recess comprises, at least in part, an annular groove for housing said ring.

In a preferred embodiment the fixing region comprises a first radially extending arm in an end region of the open ring and a second radially extending arm between the locking catch and the first radially extending arm, each arm comprising an abutment surface. The first and second radially extending arms abut opposing end walls of a slot. Thus, in this embodiment the recess comprises a slot open towards the exterior of the housing and preferably an annular groove extending about the interior wall of the bore in the plane of and in communication with the slot. The open ring is accommodated within the bore or the annular groove and the first and second radially extending arms within the slot.

In such embodiments is further preferred that the locking catch is located between the first and second radially extending arms, such that this can be deflected into the slot.

In order to enable the locking catch to smoothly disengage from the tool at the predefined torque limit, it is preferable that the locking catch comprises at least one lateral surface which is angled relative to a radial line extending from the axis of rotation, in the plane of this radial line, thus forming an inwardly tapering surface. The tapered surface may be bevelled, i.e. straight, or curved. Preferably the tapered surface is bevelled and has an angle of preferably between 30° and 60° with respect to a radial line extending from the axis of rotation, most preferably an angle of approximately 45°. The tapered surface is arranged to face in the screwing direction in which the torque must be limited, which is usually clockwise when the device is viewed from above.

The provision of the above described tapered surface usually results in a locking catch having a circumferential extent which decreases in a radially inward direction.

In use the tapered surface engages with the tool and transmits torque to this. Upon reaching the pre-determined torque limit the tapered surface will be deflected out of engagement with the tool.

Preferably the opposing lateral surface of the locking catch is non-tapered, in other words this extends approximately radially or in parallel to a radial line extending from the rotation axis. Such a non-tapered surface can transmit torque without limitation, or at least to a higher torque limit than the tapered surface, in a reverse screwing direction. This ensures that the screw can always be unscrewed from the implant analog or other component.

Alternatively the opposing lateral surface of the locking catch can form a second inwardly tapered surface, in order to provide a torque limitation for both screwing directions. The second tapered surface can have the same or a different profile to the first tapered surface such that the opposing sides can provide the same or different torque limit values.

In one preferred embodiment the torque limiting insert is shaped such that it can be operationally accommodated within the housing in two different orientations. In other words, it is preferable that the locking catch can protrude into the bore facing in either rotational direction. This is achieved by creating an insert and housing wherein the surfaces of the insert and housing which in use contact one another are symmetrical about an axis of symmetry extending through the rotation axis of the housing. This enables the insert to be inserted into the housing in both a standard orientation and a "reversed" orientation, in which the insert has been rotated 180° about the axis of symmetry.

When the locking catch has an asymmetric cross-section in a plane perpendicular to the rotation axis, the above embodiment enables a single insert of the present invention to provide two alternative torque limits to a drive tool in a single screwing direction, or alternatively, depending on the design of the insert, to have a "torque limiting" mode of operation, when a tapered surface is facing the direction of screwing, and a "no limit" mode, when a non-tapered surface is facing the direction of screwing.

The same effect can alternatively be achieved by providing a housing having a through bore, wherein the bore is capable of receiving and cooperating with a drive tool inserted through either end of the bore. In this embodiment the torque limit can be altered by changing the end of the bore into which the tool is inserted.

The torque limiting insert can be made by punching or laser-cutting a sheet of spring steel for example. Alternatively it is also conceivable to have a torque limiting insert made out of plastic and to produce it by injection molding. The housing can be machined from a blank made of stainless steel for example.

Preferably the torque limiting insert is planar, i.e. its upper and lower surfaces extend parallel to one another. This simplifies the design and manufacture of the insert and allows this to be inserted into and held within a recess having perpendicular axially limiting walls. In such embodiments, although generally planar it is possible for the upper and/or lower surfaces to include a slight inward taper or curvature at the radially inner and/or outer edge(s) of the insert. Such inward tapering does not affect the ability of the insert to be held within a recess having perpendicular axially limiting walls but can assist in manufacture of the insert.

Preferably the torque limiting insert is a monolithic structure. In other words it is integrally formed in one piece. Similarly the housing is preferably a monolithic structure. In other words it is integrally formed in one piece. In a preferred embodiment both the insert and housing are formed from a metal or metal alloy. This improves the strength and durability of the device.

It is not only the material from which the torque limiting insert is made that provides the torque limiting characteristics of the insert, but also the geometry and the thickness of the insert. These can be selected by the skilled man as necessary in order to set the desired torque limit.

Preferably the torque limiting insert is arranged to deflect into the disengaged position at a torque of below 10 Ncm, more preferably between 5 and 10 Ncm, most preferably around 8 Ncm. However, it is also possible to provide a spring insert with a higher torque limit, e.g. 35 Ncm.

In accordance with another aspect of the present invention the torque limiting device described above is part of a torque limiting kit comprising also a dental drive tool having a head fitting directly into the bore in the housing, wherein the head has at least one indent shaped to engage with the locking catch of the insert when the head is introduced in the bore, the tool further comprising drive means for transmitting torque to a third component, e.g. a screw. The locking catch transmits the torque applied to the housing to the head until the resistance of the drive tool increases such that the torque needed to rotate this further reaches a pre-determined limit. At this torque the catch is deflected out of the indent into the disengaged position, such that no further torque is transmitted to the drive tool.

In a preferred embodiment the cross-section of the indent perpendicular to the rotation axis is at least approximately rectangular, at least where the indent engages with the locking catch. Preferably the head comprises a plurality of indents spaced equally in the circumferential direction of the head, more preferably built as longitudinal grooves. The locking catch can engage with any of the plurality of indents, making the connection of the device to the drive tool a quick and simple procedure.

Preferably the upper part of the head introduced in the bore has a truncated cone shape to push the locking catch against the force of the spring region in a direction at least approximately radially outwards with respect to the rotation axis when the head is introduced in the bore. This increases the ease of insertion. When the head is further introduced in the bore, the locking catch is pushed back by the force of the spring region and engages with an indent. In some embodiments this engagement can provide an axial retention to the head in the bore.

Unlike many known dental torque wrenches, the current torque limiting device allows torque transmission in both directions. In a preferred embodiment, as discussed above, the locking catch is tapered only on one lateral surface, and thus even after the head has disengaged in the screwing direction, the torque limiting device can be used in the reverse direction to unscrew the screw.

If desired however it is possible for the locking catch to be tapered on both sides and consequently the torque can be limited in both directions.

In an alternative embodiment the cross-section of the indent perpendicular to the rotation axis has an outwardly tapered lateral surface and the lateral surfaces of the locking catch extend radially or in parallel to a radial line extending from the rotation axis in a form at least approximately rectangular.

The dental drive tool is preferably a screwdriver, most preferably a screwdriver for use with basal screws. The screwdriver preferably comprises an elongated shaft extending longitudinally from the head and having at its distal end the drive means, which preferably has a non-circular cross-section, such as a polygonal, e.g. hexagonal, or Torx® shape.

The torque limiting kit according to the present invention comprises a housing, at least one torque limiting insert and at least one drive tool.

The torque limiting kit can also comprise a plurality of interchangeable torque limiting inserts, wherein the torque limiting inserts each have a different torque limit. A preferred series of torque limiting inserts would provide individual torque controls varying from 5 to 50 Ncm, more preferably 5 to 35 Ncm. Each insert can be individually inserted into the housing, to form a torque limiting device in accordance with the present invention.

It is also the purpose of this invention to propose the use of this torque limiting kit to fasten screws to implants or implant analogs in order to connect abutments thereto. The kit could also be used to connect other dental implant components together, e.g. to screw the final or a temporary dental prosthesis to the abutment, or to screw an impression post to the implant or abutment. More generally it is intended that the torque limiting device and kit of the present invention is used to fasten together components of a dental implant system.

Preferred embodiments of the torque limiting device and of the torque limiting kit according to the invention will now be described, by way of example only, with reference to the accompanying drawings, in which.

Figure 1:
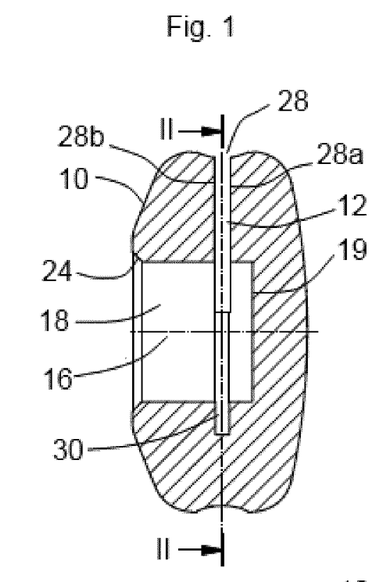
FIG. 1 shows a cross-section through a housing of a torque limiting device of the present invention, taken on the line I-I of FIG. 2.
Figures 7, 8:
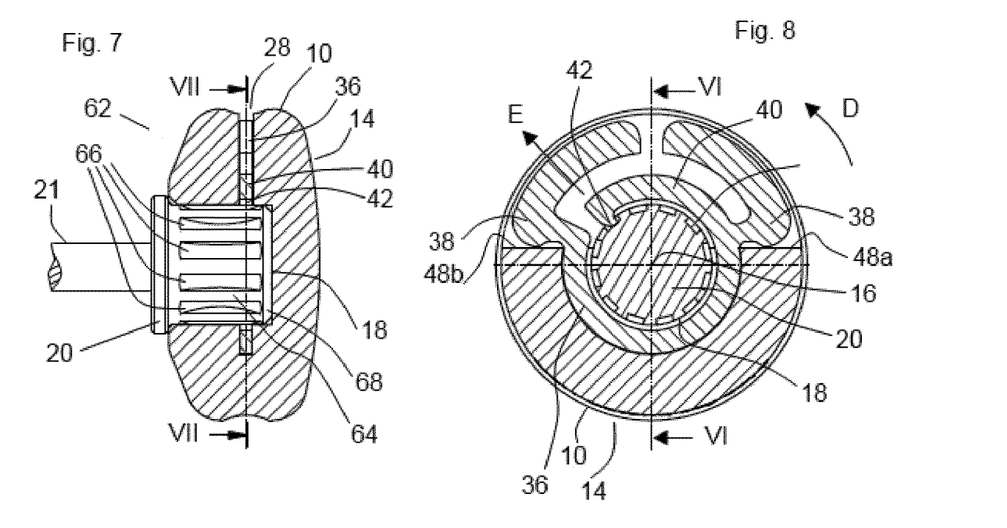
FIG. 7 shows the torque limiting device of FIG. 6 in a plane including the rotation axis taken on the line VI-VI of FIG. 7 and in which a drive tool is inserted, represented in side view.
FIG. 8 shows a cross-section through a torque limiting device in which a drive tool is inserted taken on the line VII-VII of FIG. 7.

Referring to FIG. 1, a housing 10 of a torque limiting device 14 according one embodiment of the present invention defines a rotation axis 16 and has a blind bore 18 concentric with the rotation axis 16 to directly receive a tool 20 (see FIG. 7).

The housing 10 has a chamfer 24 at the edge of the bore 18 meant to allow an easy introduction of the tool 20 and a perpendicular abutment surface 19 at the end of the bore which limits the extent to which the tool can be inserted.

The housing 10 has a recess 28 in a plane perpendicular to the rotation axis 16 comprising a slot 12, open towards the exterior of the housing 10 and in communication with the bore 18. The slot 12 is limited in the circumferential direction by end walls 48a, 48b, which in this embodiment are parallel to the diameter of the housing.

In this embodiment, the housing 10 is at least approximately in the form of a circular cylinder and the slot 12 is in the form of a circular segment 26 smaller than the respective semicircle.

The recess 28 further extends in the form of an annular groove 30 about the interior wall of the bore 18, concentrically to the rotation axis 16 of the housing 10, in the plane of and in communication with the slot 12.

In this embodiment not only is the central axis of the recess 28 perpendicular to the bore 18, but the axially limiting walls 28a, 28b also extend in a plane perpendicular to the rotation axis 16. This makes the recess 28 very simple to manufacture.

Figure 2:
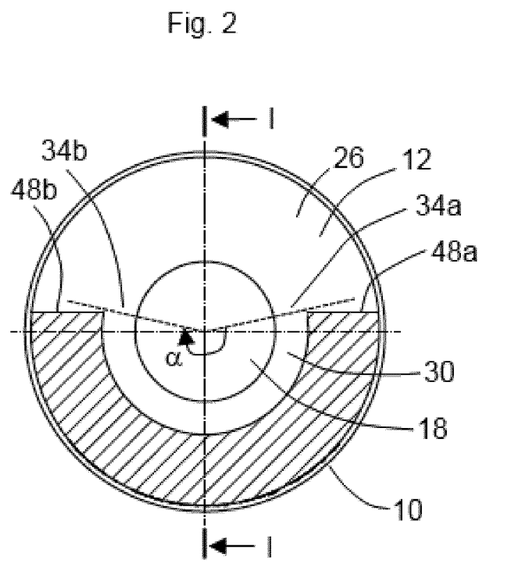
FIG. 2 shows a cross-section through the housing of a torque limiting device taken on the line II-II of FIG. 1.

As shown in FIG. 2 the annular groove 30 has an angle α of more than 180°, approximately 200° in the present embodiment, measured from one end wall 48a of the slot 12 to the other end wall 48b. The recess 28, which comprises the slot 12 and annular groove 30, is sized to allow insertion and accommodation of a torque limiting insert 36, see FIGS. 4 and 5.

Figure 3:
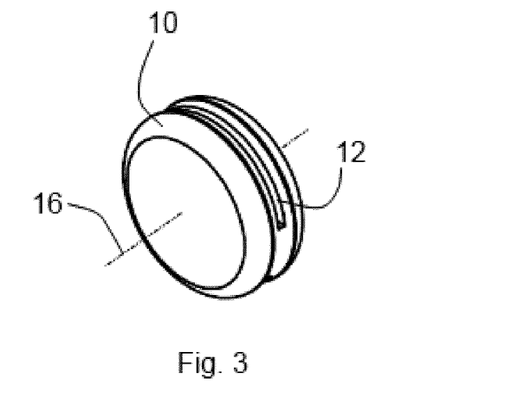
FIG. 3 shows a perspective view of the housing of FIGS. 1 and 2.

FIG. 3 shows the housing 10 of the torque limiting device 14 with the rotation axis 16 and the slot 12. In some embodiments the slot 12 can be sealed to provide a smooth exterior surface and prevent incursion of dirt into the slot.

Figure 4:
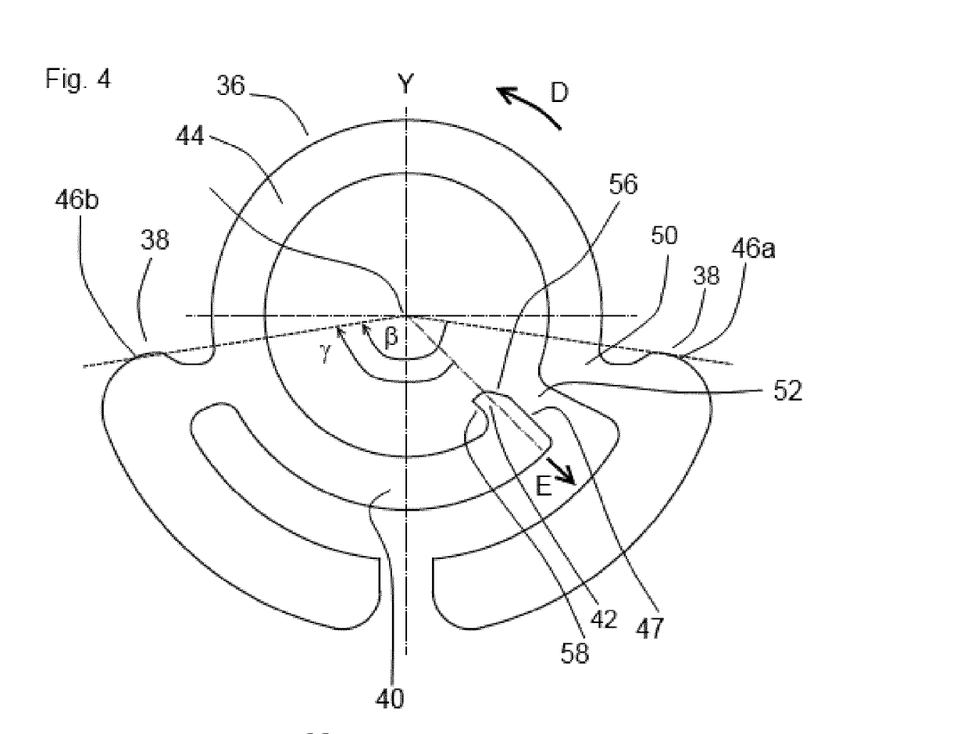
FIG. 4 shows a bottom view of a torque limiting insert of the present invention.
Figure 5:
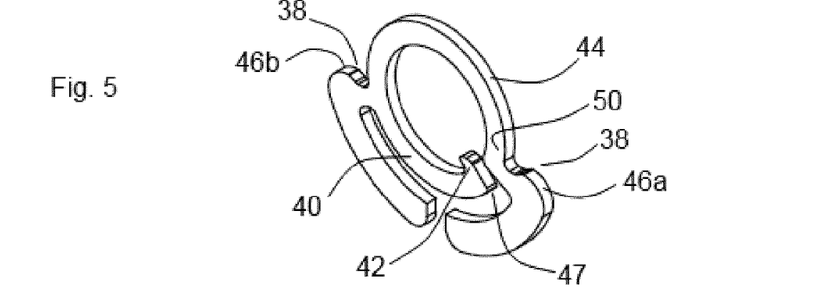
FIG. 5 shows a perspective view of the torque limiting insert of FIG. 4.

FIG. 4 shows a bottom view and FIG. 5 shows a perspective view of a torque limiting insert 36 for use with the above housing.

In this preferred embodiment the torque limiting insert 36 is substantially in the form of an open circular ring 44 comprising a fixing region 38 to fix the torque limiting insert 36 to the housing 10 in a non-rotational manner and a spring region 40 having a locking catch 42.

The open ring 44 has a locking catch 42 at one end 47 and the fixing region 38 has a first radially extending arm 46a at the other end 50 of the open ring 44 remote from the locking catch 42. The open ring 44 has a second radially extending arm 46b between the locking catch 42 and the end region 50. The second radially extending arm 46b delimits with the locking catch 42 the spring region 40 and an angle γ with respect to the rotation axis 16. In the present embodiment the angle γ is approximately 110°.

The fixing region 38 is meant to sit against the end walls 48a and 48b respectively of the slot 12. This prevents rotation of the insert relative to the housing in either direction.

The arms 46a and 46b define a circle sector with respect to the rotation axis 16 with a central angle β of less than 180°. The opening 52 of the ring 44 and the locking catch 42 are located with this angle, between the arms 46a, 46b. The arms 46a and 46b are each designed to extend in an at least approximatively radially outwards direction with respect to the rotation axis 16. These arms extend further in a circumferential direction towards each other.

The arms 46a and 46b are meant for an easy manipulation of the torque limiting insert when it is inserted into or removed from the recess 28.

The locking catch 42 is tapered on the lateral side 56 in the direction D in which the torque must be limited and extends radially on the opposing side 58 in order to transmit the torque without a limitation. In this embodiment the torque applied in the direction D will be limited and there will be no limitation in the opposite direction.

The outer shape of the insert 36 is such that this can be flipped about an axis of symmetry Y running through the rotation axis and reinserted into the housing in order to reverse the direction of screwing in which the torque limitation is applied.

In this embodiment the insert is planar such that this can be fully housed within recess 28.

Figure 6:
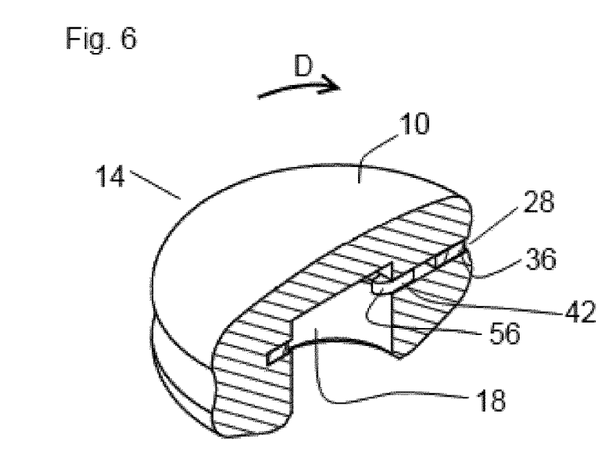
FIG. 6 shows a cross-section through a perspective view of the housing of FIGS. 1-3 and the insert of FIGS. 4 and 5 in combination.

FIG. 6 shows the insert 36 of FIGS. 4 and 5 inserted into the housing 10 of FIGS. 1-3, thus forming a torque limiting device 14 in accordance with one embodiment of the present invention. From FIG. 6 it can be seen that the insert 36 is housed entirely within recess 28 with the exception of the locking catch 42, which protrudes into the bore 18. The tapered surface 56 faces in the direction of rotation D. The locking catch 42 is in alignment with the recess 28 such that this can be deflected radially outwards into the slot 12 of the recess 28.

A torque limiting kit 62 according to the present invention comprises a housing 10, at least one torque limiting insert 36 and at least one tool 20. It can also comprise a plurality of interchangeable torque limiting inserts with each a different torque limit.

FIG. 7 shows the housing 10 with the torque limiting insert 36 inserted in the recess 28 and the tool 20 axially inserted in the bore 18. The tool 20 has a head 64 fitting directly into the bore 18 in the housing 10.

The tool 20 has a shaft 21 extending longitudinally from the head and comprising at its distal end drive means (not shown) for transmitting torque to a fastening element, e.g. a screw. The drive means can take the form of any known mechanism, e.g. a screwdriver with a Torx® or hexagonal head. Alternatively the tool 20 can comprise a central recess to receive a screw head or an abutment.

The upper part of the head 68 has a truncated cone shape meant to push the locking catch 42 against the force of the spring region 40 in a direction E at least approximately radially outwards with respect to the rotation axis when the head 64 is introduced in the bore 18. When the head 64 is further introduced in the bore 18, the locking catch 42 pushed back by the force of the spring region 40 engages with an indent 66.

The head 64 has a plurality of longitudinally extending indents 66 to engage with the locking catch 42 of the spring region 40, when the head 64 is introduced in the bore 18. As the housing is rotated in direction D (see FIG. 8) the locking catch 42 transmits the torque to the tool, which in turn transmits this to a fastening element.

When the torque needed to rotate the tool 20 increases and reaches a pre-determined limit, the spring region 40 of the insert 36 will deflect, and the locking catch 42 will be pushed out of indent 66 in the direction E, into the recess 28.

As shown in FIG. 8, the fixing region 38 of the insert 36 sits against the end walls 48a and 48b, respectively, of the slot 12 in circumferential direction. In some embodiments arms 46a, 46b exert a biasing force against end walls 48a, 48b in order to retain the insert 36 within the recess 28. In the present embodiment however the insert 36 is held within the recess 28 by an interference fit with the recess, including the axially limiting, i.e. upper and lower, walls 28a, 28b of the recess.

In the preferred embodiment shown, the cross-section of the indents 66 perpendicular to the rotation axis 16 is at least approximately rectangular, at least where the indent 66 engages with the locking catch 42. The head comprises a plurality of indents 66 spaced equally in the circumferential direction of the head 64, built as longitudinal grooves.

The housing can also comprise a lip and an undercut to form a snap-fit for the axial retention of the tool.

The above described embodiments are for illustrative purposes only and the skilled person will realize that alternative arrangements are possible which fall within the scope of the claims. For example, the insert may not comprise an open ring 44 but instead have a semi-circular or arc shape for accommodation solely within a slot. Alternatively the recess may comprise only an annular groove such that the recess is not in communication with the exterior of the housing.

REFERENCE LIST 10 housing
12 slot
14 torque limiting device
16 rotation axis
18 bore
19 abutment surface
20 tool
21 shaft
24 chamfer in the housing
26 circular segment
28 recess
28a, 28b axially limiting walls of recess
30 annular groove
36 torque limiting insert
38 fixing region
40 spring region
42 locking catch
44 open ring
46a, 46b arms
47 end of the ring
48a, 48b end walls of the slot
50 end region of the open ring
52 opening in the ring
56 side of the locking catch (with torque limitation)
58 side of the locking catch (without torque limitation)
62 torque limiting kit
64 head of the tool
66 indent in the tool
68 upper part of the head
α central angle of the annular groove
β central angle defined by the stops 46a and 46b with respect to the rotation axis 16
γ angle defined by the second stop 46b and the locking catch 42 with respect to the rotation axis 16)
D torque direction
E disengaging direction
Y axis of symmetry

The invention claimed is:

1. A torque limiting device for use with a dental drive tool comprising a housing defining a rotation axis and having a bore concentric with the rotation axis and a torque limiting insert, wherein the housing has a recess perpendicular to and in communication with the bore for housing at least a part of the torque limiting insert, the torque limiting insert comprising a fixing region held within the housing in a non-rotatable manner and a spring region extending from the fixing region and comprising a locking catch, said locking catch protruding into the bore in a resting position, and being aligned with the recess such that the locking catch can be moved at least approximately radially outwards with respect to the rotation axis into the recess in to a disengaged position, wherein the locking catch is arranged to engage with the dental drive tool when the tool is introduced in the bore in order to transmit a torque applied to the housing to the tool and to deflect into the disengaged position against the force of the spring region when a predefined torque limit has been reached.

2. The torque limiting device according to claim 1 consisting only of the housing and the torque limiting insert.

3. The torque limiting device according to claim 1, wherein the bore is a blind bore, the end surface of the bore forming an abutment surface.

4. The torque limiting device according to claim 1, wherein the recess comprises an annular groove extending about the interior wall of the bore.

5. The torque limiting device according to claim 1, wherein the recess comprises a slot open towards the exterior of the housing and limited in the circumferential direction by end walls.

6. The torque limiting device according to claim 1, wherein the recess comprises a slot open towards the exterior of the housing and limited in the circumferential direction by end walls, and an annular groove extending about the interior wall of the bore in the plane of and in communication with the slot.

7. The torque limiting device according to claim 1, wherein the fixing region of the torque limiting insert is held within the recess.

8. The torque limiting device according to claim 7, wherein the fixing region comprises two abutment surfaces which abut against opposing radially extending walls of the recess.

9. The torque limiting device according to claim wherein the recess comprises a slot open towards the exterior of the housing and limited in the circumferential direction by end walls, and wherein the fixing region comprises first and second radially extending arms, each arm comprising an abutment surface which abuts against an opposing end wall of the slot.

10. The torque limiting device according to claim 1, wherein the torque limiting insert comprises an open ring, the locking catch being located at one end and the fixing region being located at the opposing end.

11. The torque limiting device according to claim 10, wherein the recess comprises a slot open towards the exterior of the housing and limited in the circumferential direction by end walls, and wherein the fixing region comprises a first radially extending arm in an end region of the open ring and a second radially extending arm between the locking catch and the first radially extending arm, each arm comprising an abutment surface abutting an opposing end wall of the slot.

12. The torque limiting device according to claim 11, wherein the locking catch is located between the first and second radially extending arms, such that this can be deflected into the slot.

13. The torque limiting device according to claim 1, wherein the locking catch comprises at least one lateral surface which is angled relative to a radial line extending from the axis of rotation, in the plane of said radial line, thus forming an inwardly tapering surface.

14. The torque limiting device according to claim 13, wherein an opposing lateral surface of the locking catch extends approximately radially or in parallel to a radial line extending from the rotation axis.

15. The torque limiting device according to claim 1, wherein the surfaces of the torque limiting insert and housing which in use contact one another are symmetrical about an axis of symmetry extending through the rotation axis of the housing, such that the torque limiting insert is can be operationally accommodated within the housing in two different orientations.

16. The torque limiting device according to claim 1, wherein the torque limiting insert is arranged to deflect into the disengaged position at a torque of between 5 and 10 Ncm.

17. A torque limiting kit comprising the torque limiting device according to claim 1, further comprising a dental drive tool having a head fitting directly into the bore in the housing, wherein the head has at least one indent shaped to engage with the locking catch of the torque limiting insert when the head is introduced in the bore, the tool further comprising drive means for transmitting torque to a third component.

\* \* \* \* \*